United States Patent
Bracken et al.

(10) Patent No.: US 7,069,233 B2
(45) Date of Patent: Jun. 27, 2006

(54) SYSTEM AND METHOD FOR IDENTIFICATION AND NOTIFICATION OF ELEVATED OVER-THE-COUNTER MEDICATION SALES WITH RESPONSE COORDINATION

(75) Inventors: Todd C. Bracken, Indianapolis, IN (US); Kimberly Chowning, Indianapolis, IN (US)

(73) Assignee: Bracken Foster & Associates, LLC, Indianapolis, IN (US)

( * ) Notice: Subject to any disclaimer, the term of this patent is extended or adjusted under 35 U.S.C. 154(b) by 5 days.

(21) Appl. No.: 10/335,467

(22) Filed: Dec. 31, 2002

(65) Prior Publication Data

US 2004/0128184 A1      Jul. 1, 2004

(51) Int. Cl.
*G06Q 90/00* (2006.01)

(52) U.S. Cl. .................... 705/10; 705/1; 705/7
(58) Field of Classification Search ............... 700/10, 700/7, 21, 16, 30; 600/300; 705/10, 1, 2, 705/7; 340/540; 702/176–7, 179, 180, 187–8, 702/19
See application file for complete search history.

(56) References Cited

U.S. PATENT DOCUMENTS

| | | | |
|---|---|---|---|
| 4,833,600 A | 5/1989 | Brodsky | |
| 4,833,608 A | 5/1989 | Aya | |
| 5,774,875 A | 6/1998 | Medeiros et al. | |
| 5,781,893 A * | 7/1998 | Felthauser et al. | 705/10 |
| 5,946,662 A | 8/1999 | Ettl et al. | |
| 5,996,889 A | 12/1999 | Fuchs et al. | |
| 6,006,198 A | 12/1999 | Newland, Jr. | |
| 6,021,392 A | 2/2000 | Lester et al. | |
| 6,122,622 A | 9/2000 | Wiitala et al. | |
| 6,527,712 B1 * | 3/2003 | Brown et al. | 600/300 |
| 6,710,711 B1 * | 3/2004 | Berry | 340/540 |
| 2002/0004768 A1 | 1/2002 | Sekine et al. | |
| 2002/0042723 A1 | 4/2002 | Rice et al. | |
| 2002/0042762 A1 | 4/2002 | McQuade et al. | |
| 2002/0082957 A1 | 6/2002 | Krassi | |
| 2002/0087437 A1 | 7/2002 | Hogan | |

(Continued)

OTHER PUBLICATIONS

Hawkins, Dana, "Early Outbreak Alert", U.S. New and World Report, Nov. 19, 2001 [retrieved May 12, 2005], pp. 1-2, retrieved from: Dialog, file 148.*

(Continued)

*Primary Examiner*—Tariq R. Hafiz
*Assistant Examiner*—B. Van Doren
(74) *Attorney, Agent, or Firm*—Woodard, Emhardt, Moriarty, McNett & Henry LLP

(57) ABSTRACT

A system and method for identification and notification of elevated over-the-counter medication sales is disclosed. Localized alerts of elevated sales of specified over-the-counter medications and graphical views of historical sales intensity by medication category are provided. Intervention instructions to manage responses to factors causing the elevation of sales are provided. The system analyzes sales volume from stores that sell the identified medications to determine if sales volume exceeds expected thresholds. Data from individual products are combined into meaningful categories for tracking, and alerts are sent to users of data anomalies and of intervention messages or tasks requiring attention. Users view a geographic area and define their own notification events and mode. User interaction includes: a graphical representation of their geographic area with indicators of all current alerts; historical sales trend charts per category; graphical time-lapse representations of sales intensity per category; and task management to coordinate action and response.

23 Claims, 17 Drawing Sheets

U.S. PATENT DOCUMENTS

| | | | |
|---|---|---|---|
| 2002/0099598 A1 | 7/2002 | Elcher, Jr. et al. | |
| 2002/0193967 A1* | 12/2002 | Siegel | 702/187 |
| 2003/0009239 A1* | 1/2003 | Lombardo et al. | 700/30 |
| 2003/0142851 A1* | 7/2003 | Brueckner et al. | 382/107 |
| 2003/0163351 A1* | 8/2003 | Brown et al. | 705/2 |
| 2003/0177038 A1* | 9/2003 | Rao | 705/2 |
| 2003/0187615 A1* | 10/2003 | Epler et al. | 702/181 |
| 2004/0008125 A1* | 1/2004 | Aratow et al. | 340/870.07 |
| 2004/0073459 A1* | 4/2004 | Barthell | 705/2 |
| 2004/0078146 A1* | 4/2004 | Lombardo et al. | 702/19 |
| 2004/0093340 A1* | 5/2004 | Edmondson et al. | 707/101 |
| 2004/0116821 A1* | 6/2004 | Beiswenger et al. | 600/549 |

OTHER PUBLICATIONS

"The Frontlines of Medicine Project", www.frontlinesmed. org, Dec. 10, 2002 [retrieved May 12, 2005], pp. 1-3, retrieved from: Google.com and archive.org.*

"The Frontlines of Medicine Project: A Proposal for the Standardized Communication of Emergency Department Data", Annals of Emergency Medicine, Apr. 2002 [retrieved May 12, 2005], pp. 422-429, retrieved from: Google.com and archive.org.*

Gomez, Hernan F., "Report of the Frontlines of Medicine Project Consensus Conference", Frontlines Conference, Jun. 2002 [retrieved May 12, 2005], pp. 1-2, retrieved from: Google.com.*

Lombardo, Joe, et al., "Electronic Surveillance System for the Early Notification of Community-Based Epidemics", National Syndromic Surveillance Conference, Sep. 23, 2002 [retrieved May 12, 2005], pp. 1-18, retrieved from: Google.com.*

Manning, Joe, "Wisconsin Doctor Crafts Strategy for Hospitals in Case of Terrorist Attack", Knight-Rider Tribune, Apr. 15, 2002 [retrieved May 12, 2005], 2 pages, retrieved from: Dialog, file 20.*

"Biosecurity 2002 to focus on Prepardness, Biodetection, Treatment, Consequence Management", Ascribe, Jun. 28, 2002 [retrieved May 12, 2005], pp. 1-2, retireved from: Dialog, file 20.*

Eig, Jonathan, "Drugstore Data could be tip-off to bioterrorism", Wall Street Journal, Nov. 13, 2001 [retrieved May 12, 2005], 1 page, retrieved from: Dialog, file 475.*

"Rapid Syndrome Validation Project", www.eurekalert.org, Jun. 2001 [retrieved May 12, 2005], pp. 1-2, retrieved from: Google.com and archive.org.*

Morrison, Patrick, "Drug Sales could help detect attack: finding bioterrorism through cough syrup", Indianapolis Business Journal, Sep. 2, 2002 [retrieved Feb. 1, 2006], vol. 23, No. 25, 3 pages, retrieved from: Dialog, file 16.*

Walsh, Trudy, "Will Health Databases spot Bioterror Attacks", Government Computer News, Feb. 18, 2002 [retrieved Feb. 1, 2006], vol. 21, No. 4, 3 pages, retrieved from: Dialog, file 16.*

Piazza, Peter, "Detecting and Predicting Disease for Bioterror", Security Management, May. 2002 [retrieved Feb. 1, 2006], vol. 46, No. 5, 2 pages, retrieved from: Dialog, file 15.*

Rodman, Jane, et al., "Pharmaceutical Sales—a method of disease surveillance", Journal of Environmental Health, Nov. 1997 [retrieved Feb. 1, 2006], 1 page, retrieved from: Dialog, file 99.*

"Illumitek Public Health Alert System", newsreport. dewpoint.com, Dec. 6, 2001 [retrieved Feb. 1, 2006], vol. 46, Iss. 2, pp. 1-2, retrieved from: Google.com.*

Hulme, George V., et al., "Network to Bolster CDC's fight against bioterrorism", Information Week, Dec. 31, 2001 [retrieved Feb. 1, 2006], 2 pages, retrieved from: Dialog, file 15.*

"Providence Hospital Provides Reports to Department-Health", PR Newswire, Nov. 12, 2001 [retrieved Feb. 1, 2006], 3 pages, retrieved from: Dialog, file 613.*

Centers for Disease Control and Prevention, "National Electronic Disease Surveillance System", www.cdc.gov/nedss, Aug. 15, 2002 [retrieved Feb. 1, 2006], 12 pages, retrieved from: Google.com and archive.org.*

Kady, Martin, "Bioterror gives Herndon firm new focus after Sep. 11", Washington Business Journal, Dec. 14, 2001 [retrieved Feb. 1, 2006], pp. 1-2, retrieved from: Google. com.*

Beaudeau et al., "A Time Series Study of Anit-Diarrheal Drug Sales and Tap-Water Quality", International Journal of Environmental Health Research 9, 293-311 (1999).

Goldenberg et al., "Using Grocery Sales Data For The Detection of Bio-Terrorist Attacks", Center for Disease Control and Prevention, Agency for Healthcare Research and Quality, 1-28 (2001).

Goldenberg et al., "Early Statistical Detection of Anthrax Outbreaks By Tracking Over-The-Counter Medication Sales", Center for Automated Learning and Discovery and Department of Statistics, Carnegie Mellon University, vol. 99, No. 8, 5237-5240 (2002).

* cited by examiner

Profile Information — 1102

| Field | Value |
|---|---|
| First Name | John |
| Last Name | Doe |
| Title | Director |
| Organization | State Department of Health |
| Address | 111 Healthy Way |
| | Suite 500 |
| City | Indianapolis |
| State | IN |
| Postal Code | 11111-1111 |
| Direct Phone | 123-456-7890 |
| E-mail | john.doe@sdh_in.gov |

[Set Notification Events] — 1106

Notification Device Priority — 1104

| | Device | Number / Address | Attempts |
|---|---|---|---|
| 1. | Office Phone | 123-456-7890 | 2 |
| 2. | Mobile Phone | 123-456-7899 | 2 |
| 3. | BlackBerry | john.doe@blackberry.net | 1 |
| 4. | Pager | 123-456-7888 | 1 |
| 5. | Home Phone | 123-444-4444 | 1 |

[Update]

FIGURE 11

SYSTEM AND METHOD FOR IDENTIFICATION AND NOTIFICATION OF ELEVATED OVER-THE-COUNTER MEDICATION SALES WITH RESPONSE COORDINATION

TECHNICAL FIELD OF THE INVENTION

The invention generally relates to computer software and more specifically to a system and method for identification and notification of elevated over-the-counter medication sales with response coordination.

BACKGROUND OF THE INVENTION

In today's world, bio-terrorist attacks are of increasing concern, but cannot be readily detected until a late stage when it may be too late for effective intervention. Government officials, health care facilities, and the public may not detect a problem until a number of people have been affected beyond effective intervention. There is thus an increasingly important need for monitoring public illness and detecting bio-events at the earliest possible stages of exposure and initial outbreak. The present invention is directed toward meeting this need.

SUMMARY OF THE INVENTION

It is an object of the present invention to provide a computerized system and method for identification of elevated over-the-counter medication sales. It is a further object of the present invention to provide a system and method for notification and response coordination of elevated over-the-counter medication sales.

These objects and others are achieved by various forms of the present invention. According to one aspect of the invention, a system and method for providing identification and notification of elevated over-the-counter medication sales with response coordination is provided. The system and method aids in early detection of bio-events including public health outbreaks and the deliberate release of a pathogenic agent as in a bio-terrorist attack. Since bio-terrorist pathogens initially create flu-like symptoms, tracking select categories of medications designed to address those symptoms aids in early detection of public illness, including bio-events that result from a bio-terrorist attack.

Retail sales volume data of numerous over-the-counter medications are gathered from a variety of retail sales outlets. This raw data is categorized according to the chemical composition of each individual medication to allow reporting according to a variety of categorization schemes, including single-chemical (e.g. aspirin), multi-chemical (e.g. aspirin plus caffeine), simple symptom (e.g. nausea) and complex symptom (e.g. flu). The data is received from the retail sales outlets daily, with fields for the sales date, chemical composition, number of units sold and the store identification information. Supporting data is also received from the retail sales outlets daily with location information for each store, including store number, address, city, state, ZIP code, opening date and closing date. From this information, the geo-code location such as latitude and longitude for each store is derived for use in defining the store's service area. Examples of retail sales outlets include, but are not limited to, pharmacies, grocery stores, and discounters.

Simply described, the daily sales data for each store is categorized according to one or all of the categorization schemes. For each scheme, the data is transformed using a several step process so that the alert threshold for the current day can be defined. This threshold value is calculated by analyzing past sales data, accounting for fluctuations caused by changes in general store traffic, seasonal and weekly sales trends and discrete effects such as coupon drops or promotional sales. The threshold value also allows for a margin of error in the prediction process. If the current day's sales for the individual category exceed the threshold, a localized breach is noted. Not every localized breach in the data will result in the system sending an alert message to subscribers. Additional factors analyzed are the population density surrounding the retail store as well as the proximity of other retail stores and breaches that may have occurred at those nearby stores.

When an alert is generated, a message will be sent to all subscribers whose account includes the location of the store in their geographical entitlement area. In order to protect the individual retail store's privacy, alerts and messages will only refer to the store service area where the alert occurred. The store service area can include one or more zip codes and/or portions of a given zip code. Users have the ability to define their own notification methods, the addresses used for each of those methods and the preferred order of notification. Users can also define other users to act as backups if they are not able to respond quickly. The definition of the preferred order of notification and backup users is called the notification chain. Due to the critical nature of the alert information, each user will only be given a certain period of time to respond to their notification before the system advances the notification chain. This period is flexible, and in a preferred embodiment is set to 60 minutes.

When users reply, the timestamp will be recorded for use in determining response time to notifications. This timestamp will act as acknowledgement of the notification and will stop the notification chain process for that user.

In addition to early warning and notification mechanisms, the invention provides a central workspace where subscribers can access information relevant to public health even when there are no current alerts. Users can see and interact with a map representing their geographical entitlement area. They can zoom in and out in order to see data at varying levels of detail. In addition to viewing the current state of the sales data, users can view historical data in variety of formats. These formats include historical bar and line charts, historical snapshots of the graphical map interface and a time-lapse view of the intensity of sales volume and the intensity of symptoms throughout their geographic area.

According to yet a further aspect of the invention, a computerized method for identification and notification of elevated over-the-counter medication sales is disclosed that comprises: receiving retail sales data of a plurality of over-the-counter medications; organizing the retail sales data into a plurality of categories; calculating an alert threshold for at least one of the plurality of categories; detecting when the alert threshold for the at least one of the plurality of categories is exceeded; and notifying at least one subscriber that the alert threshold was exceeded.

In another aspect of the invention, a computerized system for identification and notification of elevated over-the-counter medication sales is disclosed that comprises: a subscription module for maintaining subscriber information about a plurality of subscribers; a retail chain module for tracking sales data of a plurality of over-the-counter medications for a plurality of retail stores; a categorization module for maintaining categorization information about the plurality of over-the-counter medications; a geographic entitlement module for maintaining geographic information about a plurality of geographic areas being monitored; a breach module for detecting elevated sales of at least one of the plurality of over-the-counter medications; and a notification module for sending an alert to at least one of the plurality of subscribers when a predetermined alert threshold has been exceeded.

According to yet another aspect of the invention, a computerized method for calculating alert threshold values for over-the-counter medication sales is disclosed and comprises: (A) receiving sales data of a plurality of over-the-counter medications for a plurality of retail stores; (B) normalizing the sales data; (C) estimating a future normalized sales value; and (D) calculating an alert threshold value based at least in part on the estimated future normalized sales values.

In another aspect of the invention, a method for providing early detection of public health issues is disclosed and comprises: monitoring sales of a plurality of over-the-counter medications for a plurality of geographic regions; organizing the plurality of over-the-counter medications into a plurality of categories based on a plurality of ingredients; detecting an elevation in the number of sales in at least one of the plurality of categories; analyzing the elevated sales in the at least one of the plurality of categories to determine whether an alert should be issued; and sending an alert to at least one subscriber.

In a still further aspect of the invention, a method for monitoring the intensity level of public illness is disclosed comprising: monitoring retail sales data of a plurality of over-the-counter medications; organizing the retail sales data into a plurality of categories; and presenting an intensity of the sales of at least one of the plurality of categories.

BRIEF DESCRIPTION OF THE DRAWINGS

FIG. 11 is a simulated screen of a preferred embodiment showing adding or editing a user profile.

DETAILED DESCRIPTION OF THE PREFERRED EMBODIMENTS

Figure 1:
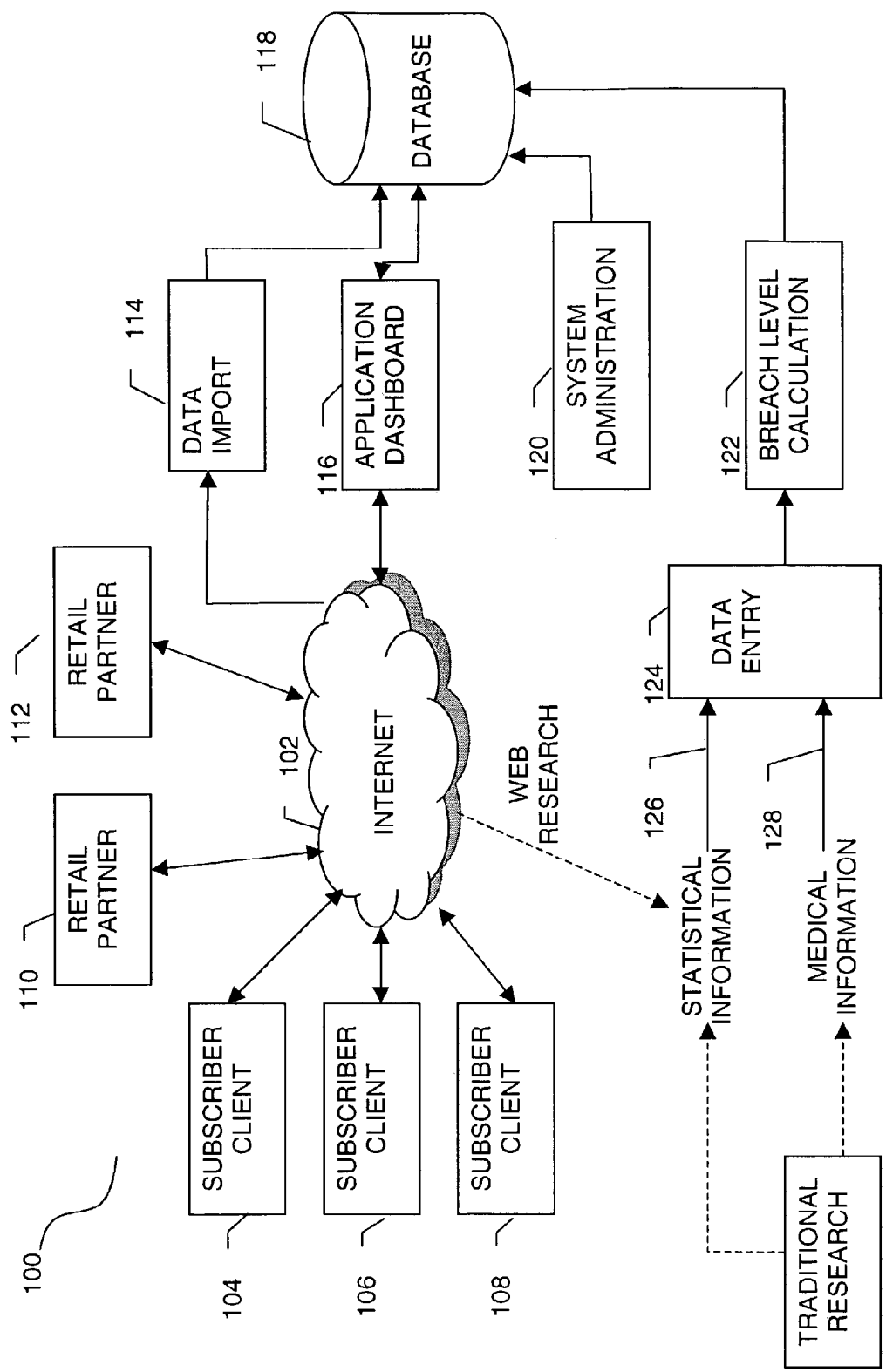
FIG. 1 is a block diagram illustrating the components of the system for identification and notification for elevated over-the-counter medication sales according to a preferred embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

The present invention provides a system and method for identification and notification of elevated over-the-counter medication sales with response coordination. The system and method aids in early detection of bio-events including public health outbreaks and the deliberate release of a pathogenic agent as in a bio-terrorist attack. Since bio-terrorist pathogens initially create flu-like symptoms, tracking select categories of over-the-counter medicines designed to address those symptoms aids in early detection of public illness, including bio-events that result from a bio-terrorist attack.

A preferred embodiment of the invention disclosed herein uses a categorization hierarchy utilizing its classification methodology and database system that organizes over-the-counter (OTC) medical products into accurate chemical, simple symptom and complex symptom classifications. The categorization hierarchy methodology, system and database also aggregate and organize OTC products by the symptoms relieved by the active ingredients (such as pain relief), as well as by the marketed purpose of those products (such as back pain relief). Over-the-counter medical products are defined herein to include traditional over-the-counter medicines such as pain relievers and upset stomach medicines, and also include other products such as facial tissue, orange juice, toilet paper, chicken soup, and herbal remedies, as a few non-limiting examples. Various products such as these that tend to serve as leading indicators of potential public illness can be monitored to help provide early detection of public health concerns.

The system communicates with each of the retail data providers who supply the retail sales data. A unique identifier (such as the UPC Code) and a base-level categorization for each OTC medication of interest are stored in a text file that is made available to the retail data providers. Each retail data provider uses the UPC codes from that file to generate a query in their database system to supply the sum of units sold in each base-level category by individual store and for a single date. The results of the query are then output into a text file, and can be structured in an XML or other text-based format.

This implementation provides several advantages. First, additional OTC medications of interest can be added to the system without requiring any retail data provider to perform additional work to maintain their database query. Second, changes to the base-level categorization scheme are easily implemented and would not cause any retail data provider to have to modify their database query. Third, each retail data provider can include any of their private label products that correspond to any of the UPC codes of the OTC medications of interest without disclosing the sales volume for their individual store brands. Fourth, proprietary information regarding volume of sales of any individual product is not made available to the system and is therefore protected from accidental distribution or unauthorized access. Lastly, gathering sales data at the base-level category allows the system to re-categorize the sales data according to a number of more meaningful categorization schemes.

Other alternate or additional methods of transmitting data from retail stores to the system are possible, such as by querying databases of the various retail data providers forming a distributed database view, by allowing the retail data providers to directly write their designated data to the database of the present system, or by utilizing one or more retail data provider clearinghouses, as a few additional non-limiting examples.

A preferred embodiment of the invention provides an automated analysis and cross-referencing system of retail sales data of OTC medical products. The system analyzes retail sales data for anomalies in daily sales numbers of a variety of categories of products. The system further analyzes those identified data anomalies to determine if there is a geographical or recurring pattern to the data anomalies. Any such pattern may be determined to be an Alert and will generate an Alert Notification to be sent to all subscribers whose subscription covers the location of the data anomaly.

FIG. 1 illustrates the system 100 of a preferred embodiment of the present invention. The system 100 operates over the Internet 102 and can support the informational needs of a plurality of subscribers 104, 106, and 108. The system 100 can accept sales data from a plurality of retail data providers 110 and 112. A data import process 114 interfaces the retail data providers 110 and 112 with a database 118. The data import process 114 reads text files provided by the retail data providers 110 and 112 and populates the database 118 with that data. An application dashboard 116 appears as a Web page and interfaces network clients 104, 106 and 108 with the database 118. A system administration utility 120 appears as a Web page and provides a mechanism for maintaining information about the subscriber clients 104, 106 and 108 and retail data providers 110 and 112 in the database 118. Statistical information 126 and medical information 128 about over-the-counter medical products, sales trends and alert levels are input through a data entry system 124 to a breach level calculation process 122. The statistical and medical information 126 and 128 can come from Web-based research or traditional research based on documents and publications. The breach level calculation 122 analyzes data in the database 118 according to the statistical and medical information 126 and 128 to determine alert levels for the data.

Such database 118 is useful in the analysis of sales trends of over-the-counter medical products through the use of database relationships that are based on chemical and symptom categories. Users are able to view comprehensive sales trend data by single-chemical, simple symptom and complex symptom categories. Users can also obtain current and historical information about alerts generated within each of those categories. Database 118 preferably allows users to conduct queries by searching on individual or multiple categories and time scales. The queries will usually take the form of system-defined charts and list selections rather than free-form entry.

A database 118 provides quantitative data for over-the-counter medical products and the sales trends of those products in a single source accessible via the Internet. Database 118 supports single-chemical, multi-chemical, simple symptom and complex symptom categories based on identified over-the-counter medical products. Queries through the Internet 102 allow users to see sales trend information for each of those category schemes.

The proper calculation of alert levels according to the variety of categorization schemes is essential for accurate notification of unusual data occurrences. The breach level calculation 122 forecasts the next time period's sales number and a threshold for each of the categories in every categorization scheme for each retail store location. In a preferred embodiment, the time period is one day. If the actual sales number exceeds the threshold, the breach level calculation 122 notes the data anomaly. Once all categories, schemes and stores are processed, the individual data anomalies are analyzed to determine the severity of the anomaly and the proximity of other anomalies. Based on this analysis, the breach level calculation 122 stores the alert information in the database 118.

In a preferred embodiment, access to the system is by subscription. Subscriptions to the system can be provided for free or upon payment of one-time or ongoing fees, as a few examples. Each customer has up to N Accounts in the system. N is controllable, and in a preferred embodiment is set to 1. Each Account has one or more Administrators who create individual Subscriber records for each person associated with that customer who will have access to the system. The number of Subscribers allowed for each Account is controllable, and in a preferred embodiment is unlimited.

In a preferred embodiment, each Account has an associated Geographical Entitlement Area. A Geographical Entitlement Area is a contiguous area defined by common governmental boundaries (e.g. ZIP codes, Counties, States) that cover an area of concern to the customer with the Account. In a preferred embodiment, Geographical Entitlement Areas are pre-defined as groups of one or more ZIP codes that conform to a variety of governmental boundaries such as Counties, Metropolitan Statistical Areas (MSAs) and States. Other Geographical Entitlement Areas that do not conform to a governmental boundary can be created to satisfy requirements of individual customers. Alert Notifications are sent only to those Subscribers whose Geographical Entitlement Area encompasses the location of the Alert.

Figure 2:
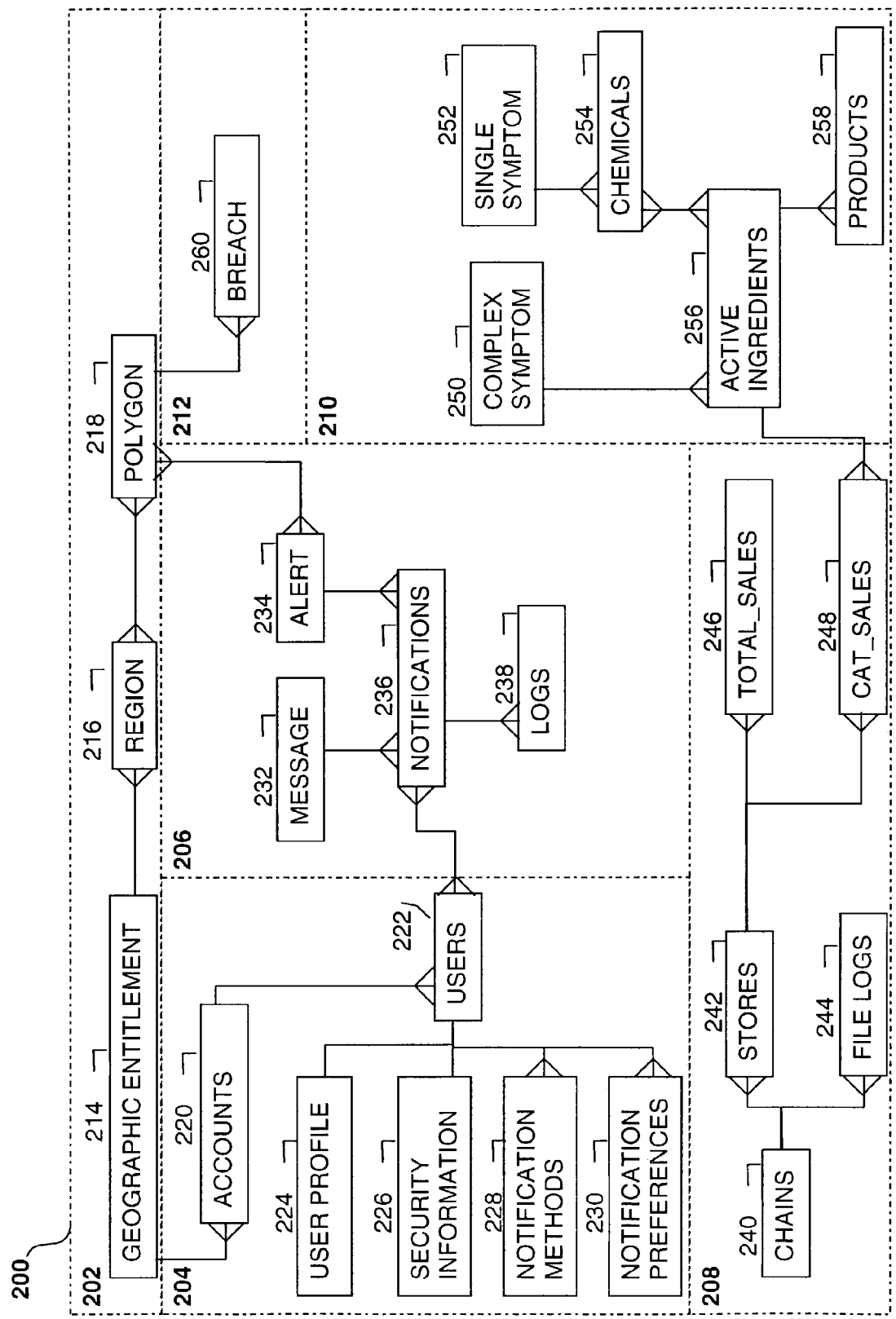
FIG. 2 is a conceptual diagram of the modules of the system for identification and notification for elevated over-the-counter medication sales according to a preferred embodiment.

FIG. 2 illustrates a conceptual diagram of a preferred embodiment of the present invention, and is referred to herein by the general reference numeral 200. The conceptual diagram illustrates a geographical entitlement module 202, a subscription module 204, a notification module 206, a retail chain module 208, a breach module 212, and a categorization module 210. Additional modules may be defined to support the functionality defined for this invention.

The geographical entitlement module 202 comprises the tables and functionality necessary to maintain information about polygons 218, region definitions 216 and geographic entitlements 214. Geographic entitlements 214 are combinations of regions 216 and are used to define the viewable data for each subscription 220. Regions 216 are combinations of polygons 218. Polygons 218 can be recognized governmental boundaries (e.g. zip codes, townships, counties) or arbitrary boundaries and are displayed on a map using Geographic Information System (GIS) technology. Polygons 218 may also represent the service area of individual stores based on their geo-code location (latitude and longitude). Alerts 234 are generated and displayed for individual polygons 218. Additional tables and functionality may be added to this module to support the defined invention.

The subscription module 204 comprises the tables and functionality necessary to maintain information about accounts 220, users 222, user profiles 224, security information 226, notification methods 228, and notification preferences 230. Each account 220 contains information about point of contact, subscription start and end dates, number of allowed users and several other pieces of information about each account. Each account 220 can have more than one user 222. Each user 222 comprises several parts. Only users defined in subscription module 204 can act as subscriber clients 104, 106 and 108 (FIG. 1). Name, address and contact information is found in the user profile 224. User ID and password are found in security information 226. Notification methods (e.g. email address, telephone number, pager number) and a schedule for notification options are found in notification methods 228. User preferences regarding what topics or alerts should generate notifications are found in notification preferences 230. Additional tables and functionality may be added to this module to support the defined invention.

The notification module 206 comprises the tables and functionality necessary to store messages 232, alerts 234, notifications 236, and logs 238. Messages 232 are created by subscribers to be sent to certain other subscribers. Messages 232 are combined with user notification preferences 230 and a delivery timestamp to create a notification 236. Alerts 234 are created by the system to indicate a breach condition exists in a particular polygon. Alerts 234 are combined with user notification preferences 230 and a delivery timestamp to create a notification record 236 to be sent to every user 222 whose geographic entitlement area 214 encompasses the polygon 218 generating the breach 250. Logs 238 are maintained of every notification 236 sent as well as confirmation of receipt from each user 222 who was sent the notification 236. Additional tables and functionality may be added to this module to support the defined invention.

The retail chain module 208 comprises the tables and functionality necessary to maintain information about retail chain data providers 240, the individual stores reported by each chain 242, the overall daily sales data for each store 246, and the categorized daily sales for each store 248. In addition, logs 244 are maintained for each file created by a retail data provider 110 and 112 (FIG. 1) over the Internet 102. Store 242 information includes location information such as address, city, state and zip code as well as derived geo-code information such as latitude and longitude. Categorized daily sales 248 are categorized according to the combination of active ingredients 256 found in individual products 258. This module contains an algorithm for sending to each retail data provider a text file containing the identification and categorization information regarding one or more of the OTC products for which they are to submit sales data. This module also contains the algorithm for importing and processing the one or more text files containing the sales data that are received from one or more retail data providers. Additional tables and functionality may be added to this module to support the defined invention.

The categorization module 210 comprises the tables and functionality necessary to maintain information about each OTC product 258, and a basic categorization of those products 258 based on the combination of active ingredients. The combination of active ingredients relieves a particular set of symptoms, referred to as complex symptoms 250. Also included is information about individual chemicals 256, and simple symptoms 254 relieved by the individual chemicals 256. This module contains an algorithm for dynamically creating the text file containing the identification and categorization information regarding one or more of the OTC products being monitored. As previously discussed, the text file then gets sent by the retail chain module 208 to the retail data providers indicating for which OTC products they should submit sales data. Additional tables and functionality may be added to this module to support the defined invention.

The breach module 212 contains the tables and functionality necessary to calculate a breach 260, or indication of abnormal sales volume. Breaches 260 are calculated for each store 242 individually. Sales volume for each store is analyzed in a number of categories (active ingredient combination 256, single chemicals 254, complex symptom 250 or simple symptom 252) to determine if a particular day's sales are abnormal. If abnormal sales levels are located, a breach record is created indicating the date, store, category and intensity of the breach. Breaches at individual stores are combined with stores appearing in the same polygons 218 to determine how many alerts 234 will be created. Additional tables and functionality may be added to this module to support the defined invention.

Figure 3:
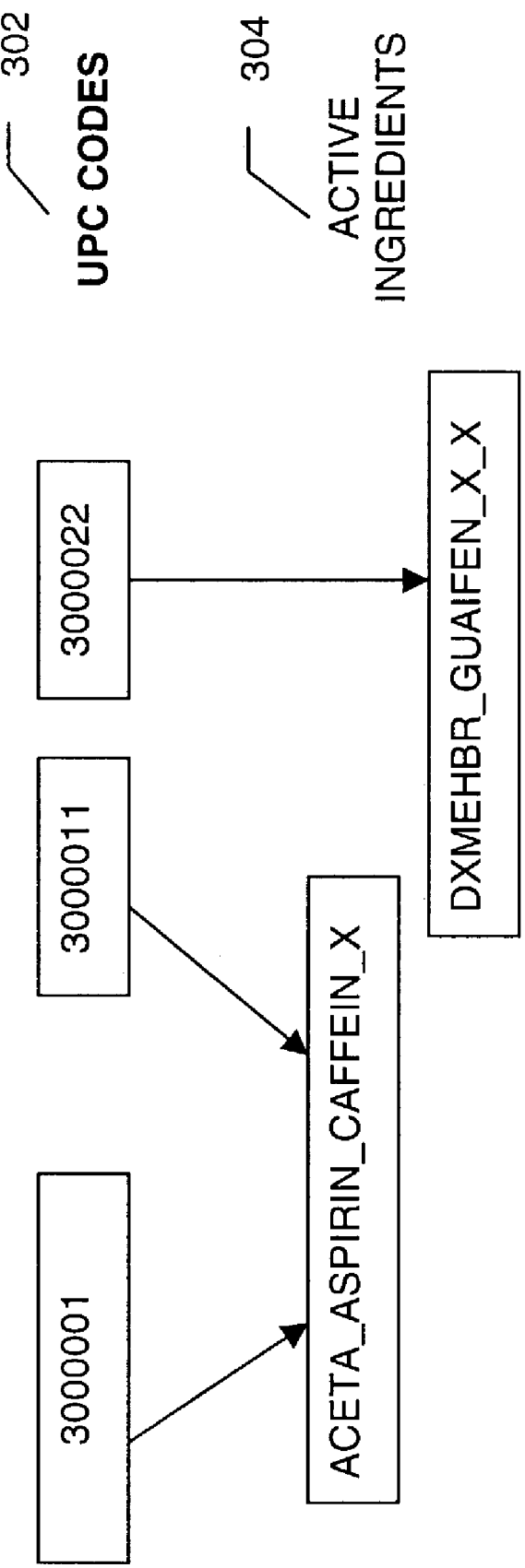
FIG. 3 is a block diagram of a preferred embodiment illustrating the single-chemical categorization methodology of the invention at its top level.

Shown in FIG. 3 is a multi-chemical categorization at its top level 302 representing the individual OTC medical products, identified by their UPC code. Each product 302 is linked to a multi-chemical category 304 representing the active ingredients found in the product. Each multi-chemical category 304 tracks up to four active ingredients for each product 302, separated by an '_'. If there are fewer than four active ingredients in a product, an 'x' is used as a placeholder. Each product 302 can have a single multi-chemical category 304. Each multi-chemical category 304 can have more than one product 302 associated with it.

Figure 4:
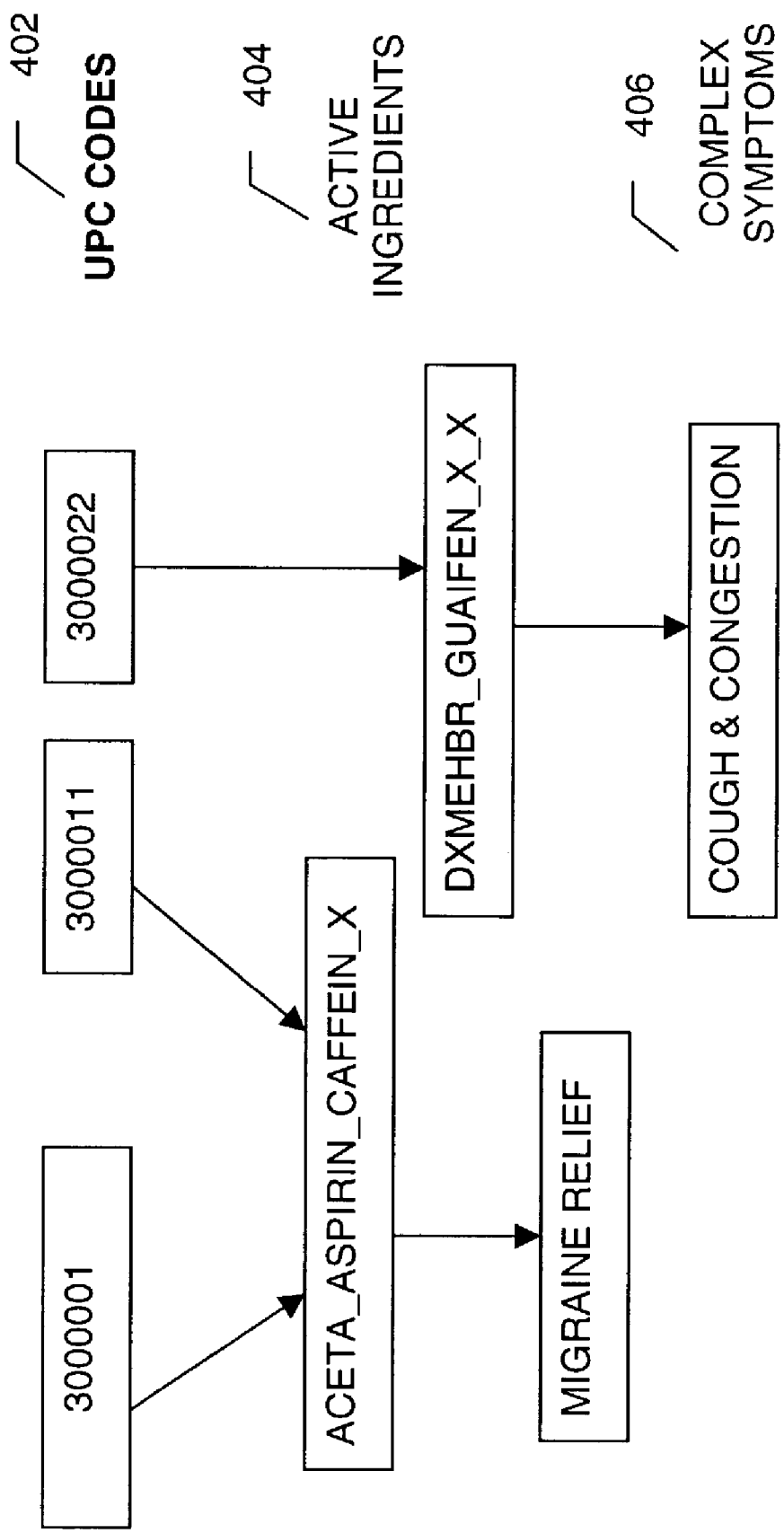
FIG. 4 is a block diagram of a preferred embodiment illustrating the simple symptom categorization methodology of the invention at its top level.

FIG. 4 illustrates the complex symptom categorization methodology of a preferred embodiment of the invention. At the top level 402 are individual OTC medical products, identified by their UPC code. Each product 402 is linked to a multi-chemical category 404 representing the active ingredients found in that product. Each multi-chemical category 404 is linked to a complex symptom 406. The complex symptoms are defined by the intended medical use of the combination of active ingredients 404.

Figure 5:
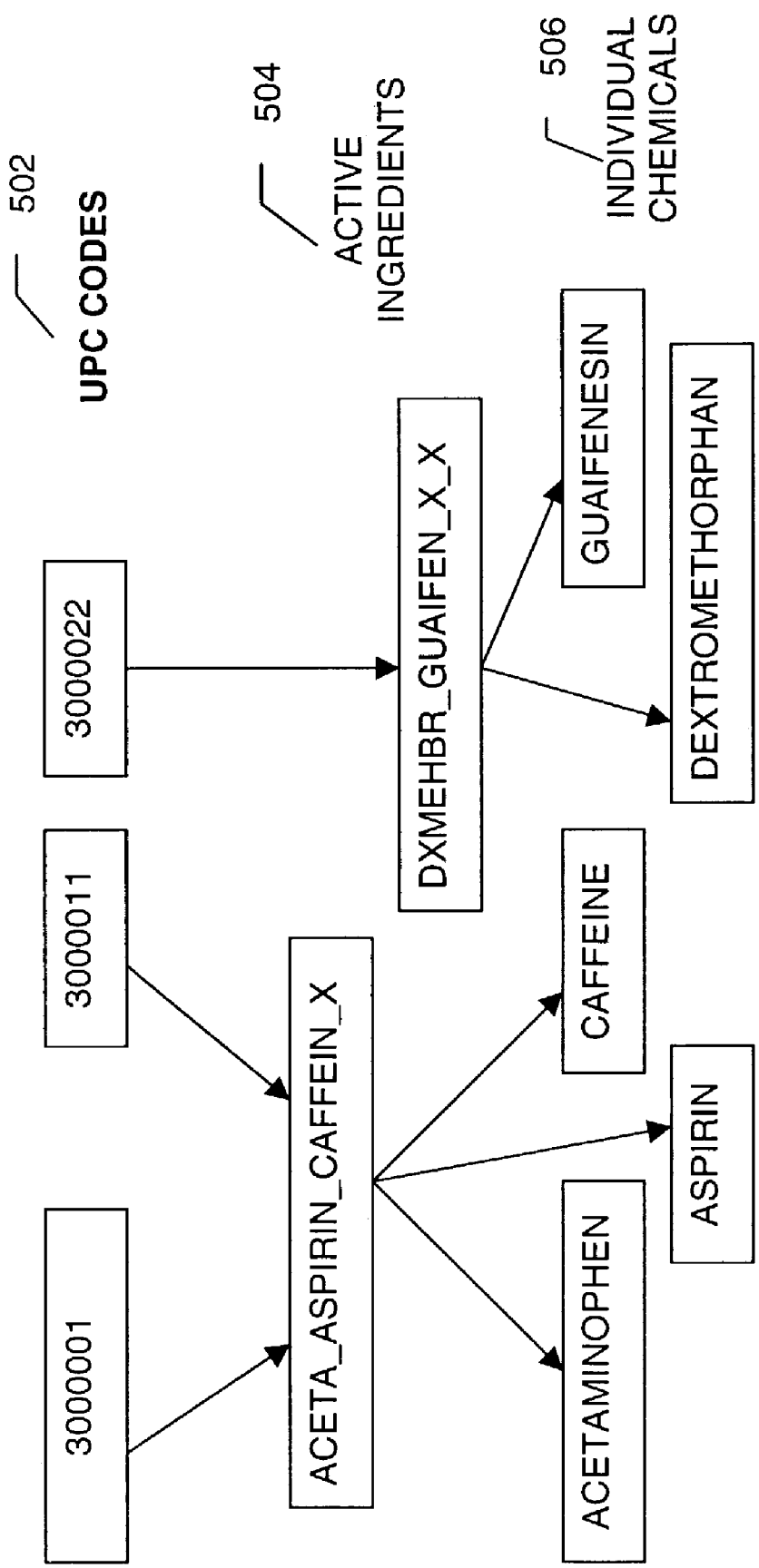
FIG. 5 is a block diagram of a preferred embodiment illustrating the multi-chemical categorization methodology of the invention at its top level.

FIG. 5 illustrates the single chemical categorization methodology of a preferred embodiment of the invention. At the top level 502 are individual OTC medical products, identified by their UPC code. Each product 502 is linked to a multi-chemical category 504 representing the active ingredients found in that product. Each multi-chemical category 504 tracks up to four active ingredients for each product 502, separated by an '_'. If there are fewer than four active ingredients in a product, an 'x' is used as a place-holder. Each multi-chemical category 504 is linked to up to four individual chemicals 506. Any place-holders found in the active ingredients 504 are not linked to individual chemicals 506. Each product 502 can have a single multi-chemical category 504. Each multi-chemical category 504 can have up to four individual chemicals 506.

Figure 6:
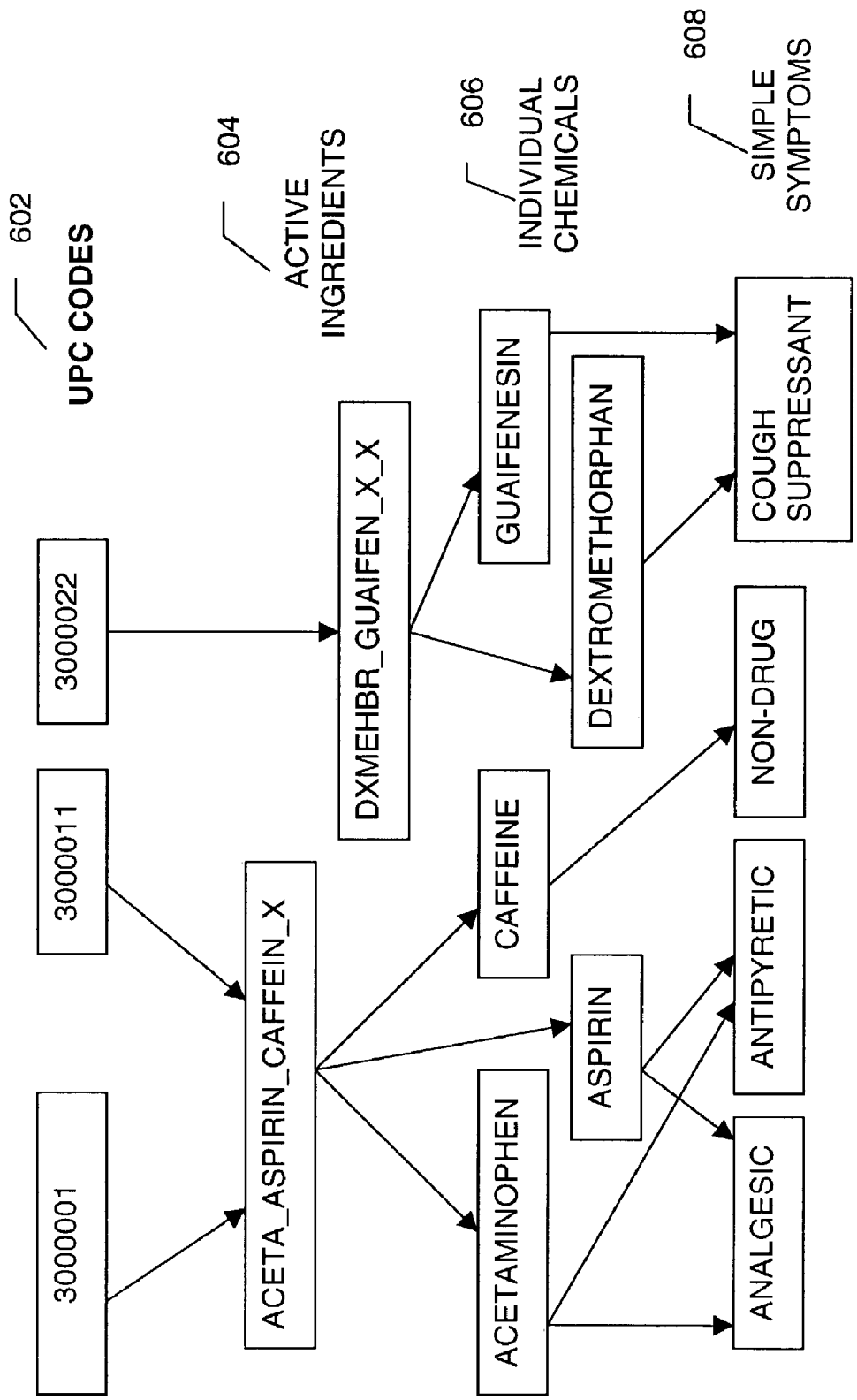
FIG. 6 is a block diagram of a preferred embodiment illustrating the complex symptom categorization methodology of the invention at its top level.

FIG. 6 illustrates the simple symptom categorization methodology of a preferred embodiment of the invention. At the top level 602 are individual OTC medical products, identified by their UPC code. Each product 602 is linked to a multi-chemical category 604 representing the active ingredients found in that product. Each multi-chemical category 604 tracks up to four active ingredients for each product 602, separated by an '_'. If there are fewer than four active ingredients in a product, an 'x' is used as a place-holder. Each multi-chemical category 604 is linked to up to four individual chemicals 606. Any place-holders found in the active ingredients 604 are not linked to individual chemicals 606. Each individual chemical 606 is linked to one or more simple symptoms 608 based on the intended medical use of each individual chemical. Each product 602 can have a single multi-chemical category 604. Each multi-chemical category 604 can have up to four individual chemicals 606. Each individual chemical 606 can be linked to one or more simple symptoms 608.

It will be recognized by those in the art that various other categorization schemes are possible and would still be within the spirit of the invention.

Figure 7:
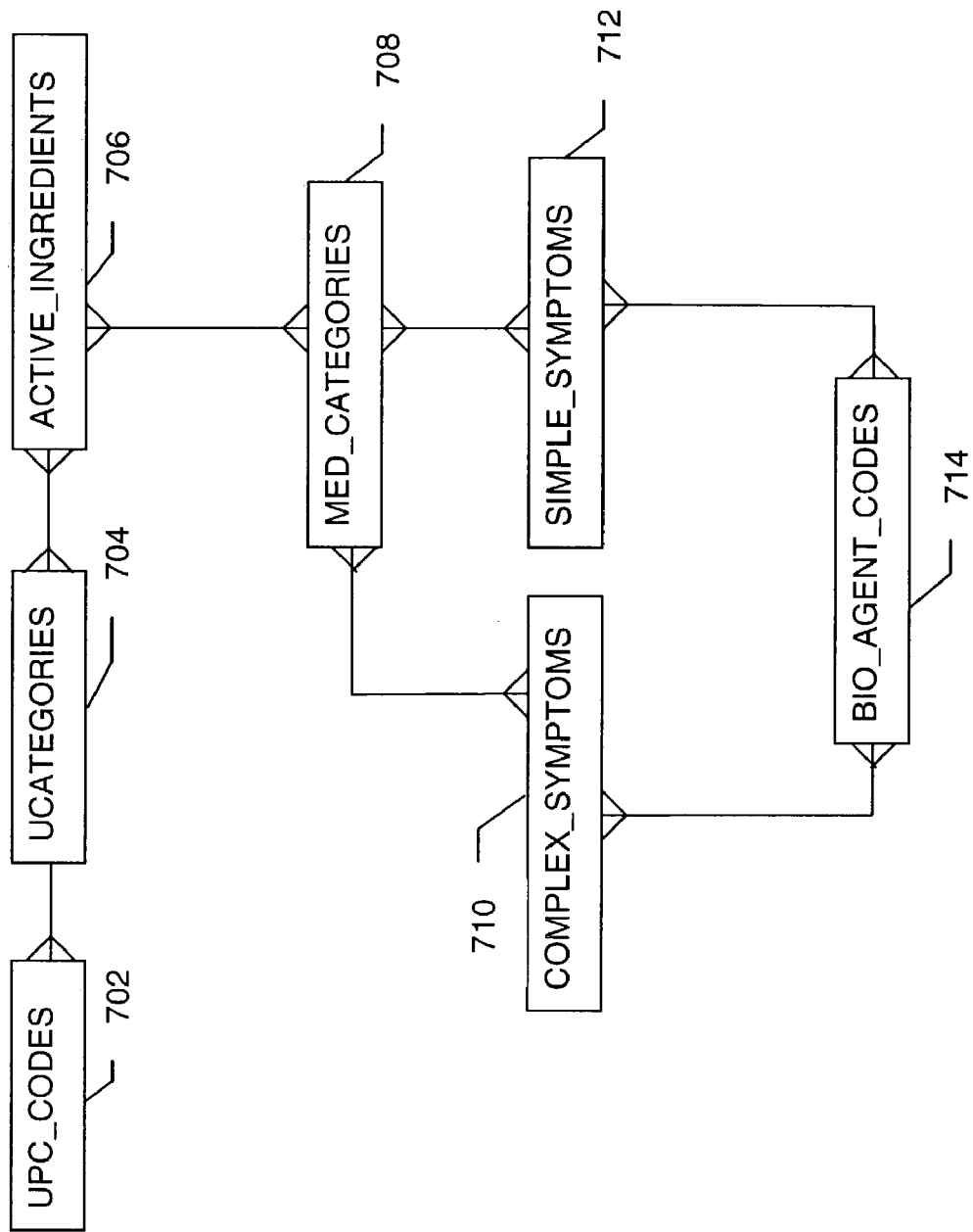
FIG. 7 is a block diagram of a database structure of a preferred embodiment that allows the building of the multiple categorization schemes where individual products can be related to any or all of the categorization methodologies.

FIG. 7 illustrates how individual OTC medical products 702 can be related to any or all of the categorization methodologies described in FIGS. 3, 4, 5 and 6.

Figure 8:
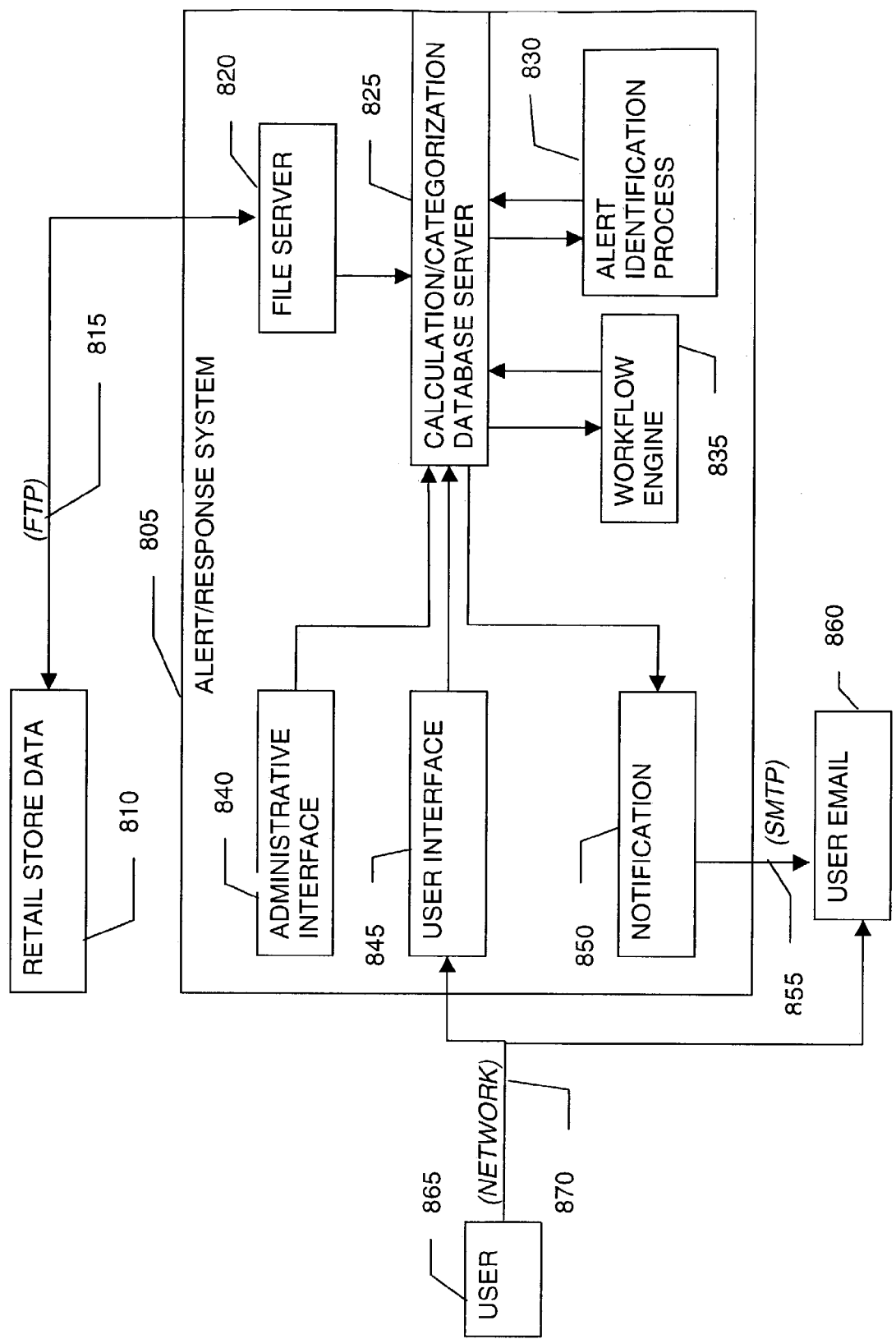
FIG. 8 is a block diagram of the main components according to a preferred embodiment.

FIG. 8 is a block diagram of the main components, according to a preferred embodiment of the invention. An alert/response system 805 comprises an administrative interface 840 and user interface 845, both of which have access to the calculation/categorization database system 825. In a preferred embodiment, the calculation/categorization system is implemented in a computerized database system. A user 865 defines their profile and notification chain according to the invention using the alert/response system user interface 845 over a network 870. In a preferred embodiment, the network 870 is an Internet connection and the alert/response system 805 comprises a production software application accessible over the World Wide Web. Retail data providers receive a text file containing identification and categorization information regarding one or more of the OTC products being monitored. Retail data providers transfer retail store data 810 to a file server 820 using an FTP connection 815. The data from the file server 820 is imported into the database 825. Each day, an alert identification process 830 examines the retail store data to define alert levels and to create notification records. A workflow engine 835 stores tasks and approvals required to respond to any alerts. Users 865 can interact with the workflow engine 835 through the user interface 845 and the database server 825. The workflow engine 835 creates notification messages if there are tasks or approvals requiring action from the user 865. Each day, a notification process 850 sends pending notifications to the user's email account 860 using SMTP 855. It should be appreciated that the notification can be sent to any specified email account or to any other supported notification method. It should be appreciated the multiple notifications can be sent to a single user, and it should be appreciated that the user can browse existing notification messages in the system 805.

Figure 9:
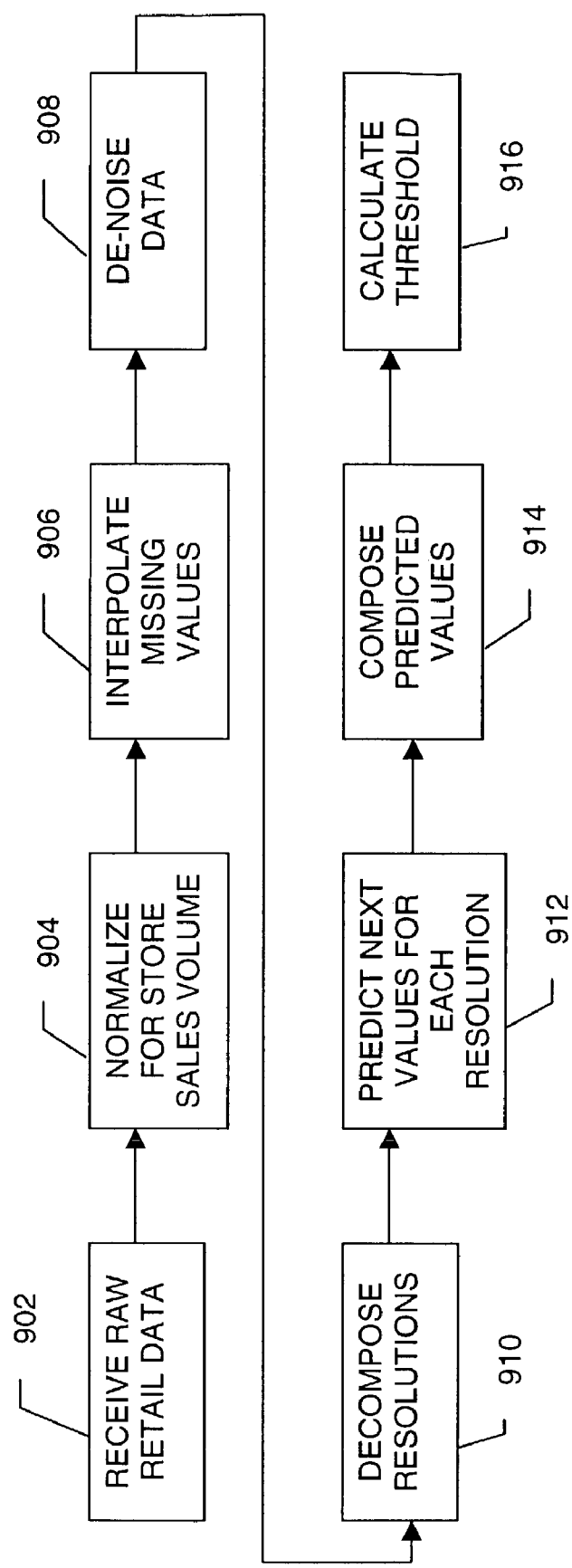
FIG. 9 is a block diagram of a preferred embodiment process for transforming the data used to define the alert threshold value.

FIG. 9 is a block diagram of a preferred embodiment process for transforming the data used to define the alert threshold value. Sales data 902 is received from retail data providers 110 and 112 (FIG. 1) each day. The data is normalized for overall store sales volume 904 by dividing the number of units sold in each OTC medical category by the overall number of units sold at the store. Any missing data values are extrapolated 906 from surrounding days. Data may be missing because a store was closed on a particular day or a data file was not received from the retail data provider or for other reasons. The normalized and extrapolated data is "de-noised" 908 by using a discrete cosine transformation that smoothes the extreme values of the data series while retaining the overall shape of the series. The resulting data series is decomposed into its component resolutions 910 by using a discrete (redundant) wavelet transformation. The component resolutions describe different frequencies of the original data series. For each component resolution, the next day's value is calculated 912 using simple autoregressive models. The predicted values are summed 914 to provide a predicted value for the next day's normalized sales value. The alert threshold is calculated 916 as a number of standard deviations above the average for the data series. The number of standard deviations is controllable, and in a preferred embodiment is set to three. Any number of methods could be used to accurately predict the next day's sales value and define a threshold for alert. The next figure describes an alternate method.

Figure 10:
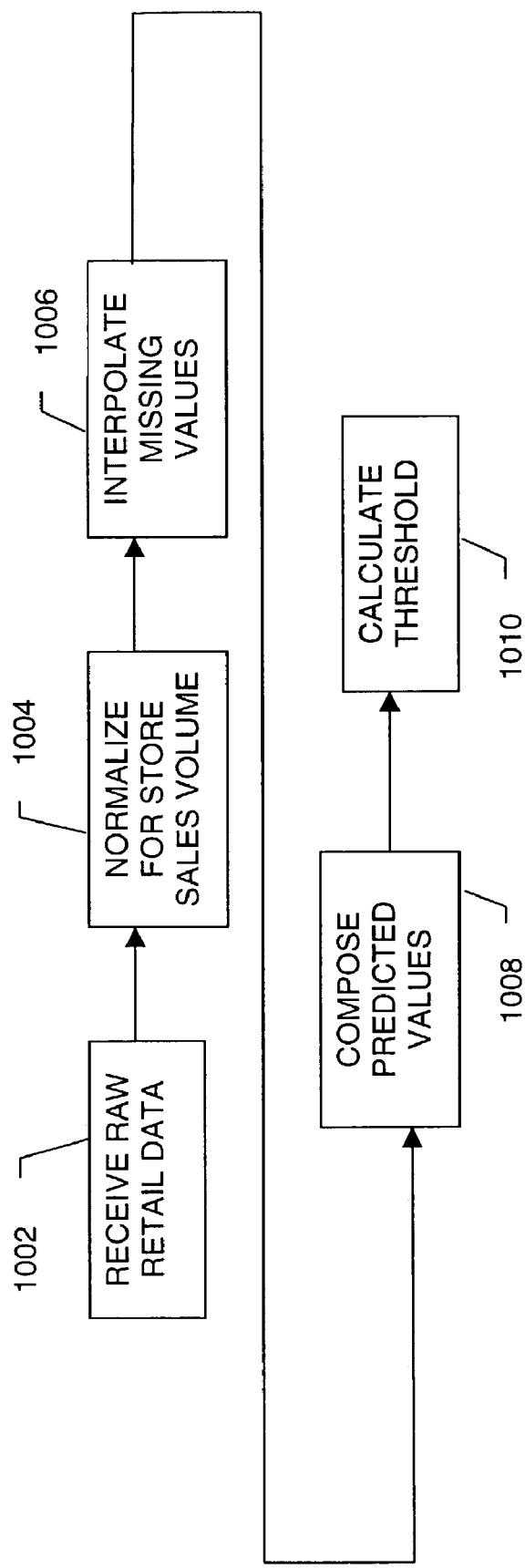
FIG. 10 is a block diagram of an alternate embodiment process for transforming the data to define the alert threshold value.

FIG. 10 is a block diagram of an alternate embodiment of the data transformation process used to define the alert threshold value. Sales data 1002 is received from retail data providers 110 and 112 (FIG. 1) each day. The data is normalized for overall store sales volume 1004 by dividing the number of units sold in each OTC medical category by the overall number of units sold at the store. Any missing data values are extrapolated 1006 from surrounding days. Data may be missing because a store was closed on a particular day or a data file was not received from the retail data provider or for other reasons. For each weekday, the next value for that same weekday is predicted 1008 by averaging the values of the actual sales for each of the same weekdays in the past. For example, if the next day is a Monday, then all actual values for all Mondays in the database are averaged to provide the predicted value for the next day. The alert threshold is calculated 1010 as a number of standard deviations above the average for the data series. The number of standard deviations is controllable, and in a preferred embodiment is set to three. Any number of methods could be used to accurately predict the next day's sales value and define a threshold for alert.

FIG. 11 shows a simulated screen that allows adding or editing a subscriber profile. A subscriber might be, for example, an employee of a government agency, a public or private health care facility, or anyone who has permission to access the system. A subscriber could also be a member of the general public. In a preferred embodiment, each Subscriber is a member of a single Account. A Subscriber maintains their own Profile 1102, including contact information such as name, address and telephone number, as well as notification information such as addresses and priority preferences. The notification information 1104 defined by each Subscriber is referred to as their Notification Chain. In a preferred embodiment, the supported notification methods include email, telephone, pagers, cell phone messages, fax, and voice. Additional notification methods are possible, including the option to notify another subscriber.

In a preferred embodiment, the Notification Chain is used whenever an Alert Notification or Proactive Notification is sent. In a preferred embodiment, a Subscriber is able to define the specific events to receive proactive notification 1106, as will be discussed with reference to FIG. 12. Each Subscriber is contacted using their preferred notification method and address. If the Subscriber has not responded to that notification within the defined number of attempts, their next notification method is used. This process repeats until all notification methods for that Subscriber are exhausted. The time allowed for a Subscriber to respond before the Notification Chain is advanced is controllable, and in a preferred embodiment is set to one hour. In a preferred embodiment, a Subscriber can respond to a Notification by logging into the system. Alternatively or additionally, a user can respond to a Notification by verbally responding to a telephone notification, responding to a telephone notification by entering an identification code, replying to an email received by the system, or calling into a call center to confirm receipt of the notification, as a few non-limiting examples. The response method that is required can optionally be varied depending on what type of notification method was used to send the alert at the particular level of the notification chain.

Figure 12:
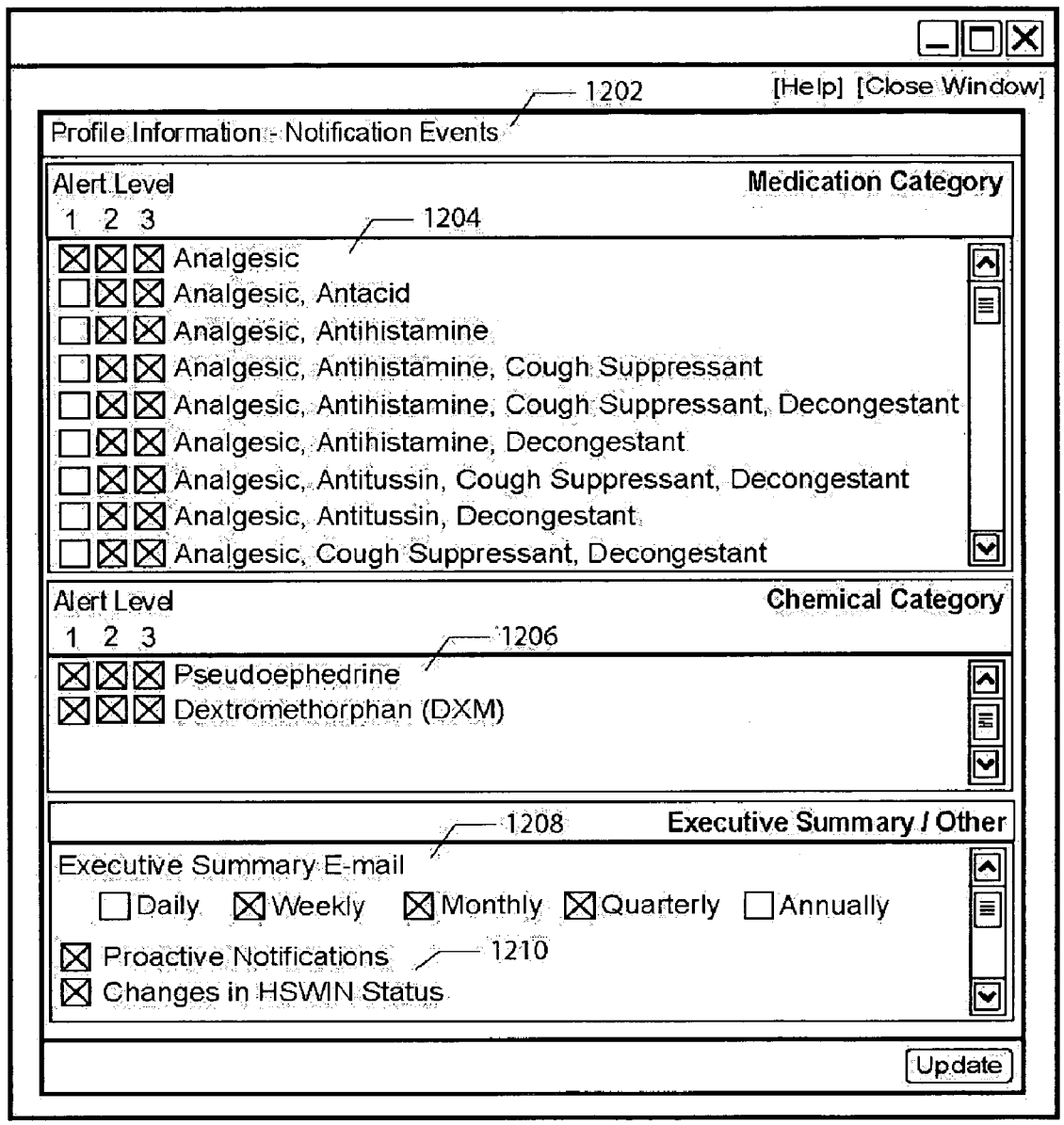
FIG. 12 is a simulated screen of a preferred embodiment showing adding or editing notification events for a user profile.

FIG. 12 shows a simulated profile screen for designating the notification events for a particular Subscriber. In a preferred embodiment, each Subscriber is able to select the desired alert event and alert level 1202. This can be done by Medication Category 1204 and Chemical Category 1206. The Subscriber also defines other notifications preferences such as the preferred frequency to receive activity summary e-mails 1208 and other system generated events that activate proactive notification 1210.

In a preferred embodiment, each Subscriber is assigned to one of several User Roles that govern their level of access to the system. The possible User Roles are: Super User, Account Administrator, Approver, Author and User. Additional User Roles can be created to address the requirements of the system. A Super User can create, update and deactivate Account, Subscribers and User Roles. An Account Administrator can modify their account's Subscriber information and may create or deactivate Subscribers within their Account. An Approver may approve any alert messages prior to the notifications being sent to the Subscribers. An Author may create and send messages via the system. A User is a generic user, with no special permissions or capabilities beyond the default functionality of the system.

In a preferred embodiment, there are three types of Notifications: Passive, Proactive and Alert. Passive Notifications are created by an Author and are simply displayed within the system to all Subscribers entitled to see the Notification. No attempt is made to notify the Subscriber outside of the system. Proactive Notifications are also created by an Author and displayed within the system, but the Notification Chain is activated for each Subscriber. Alert Notifications are generated by the system in response to the Alerts identified by the analysis process. Alert Notifications are also displayed within the system and activate the Notification Chain for each Subscriber In a preferred embodiment, Subscribers will receive Alert Notifications whenever an Alert is validated in their Geographical Entitlement Area. The message sent in the Alert Notification is controllable, and in a preferred embodiment provides the subscriber with basic information regarding the bio-event or notification. Subscribers are urged to log into the system where they are shown details of the data anomaly, including its severity and location.

In a preferred embodiment, Subscribers are able to log into the system at any time, regardless of whether there have been recent Alert Notifications. Whether there are Alert Notifications or not, Subscribers will be able to interact with the system to view their Geographical Entitlement Area, recent and historical information about Alerts, charts of sales trends for a variety of OTC medical categories, a workflow engine for managing tasks and assignments and additional functionality provided by the system.

Figure 13:
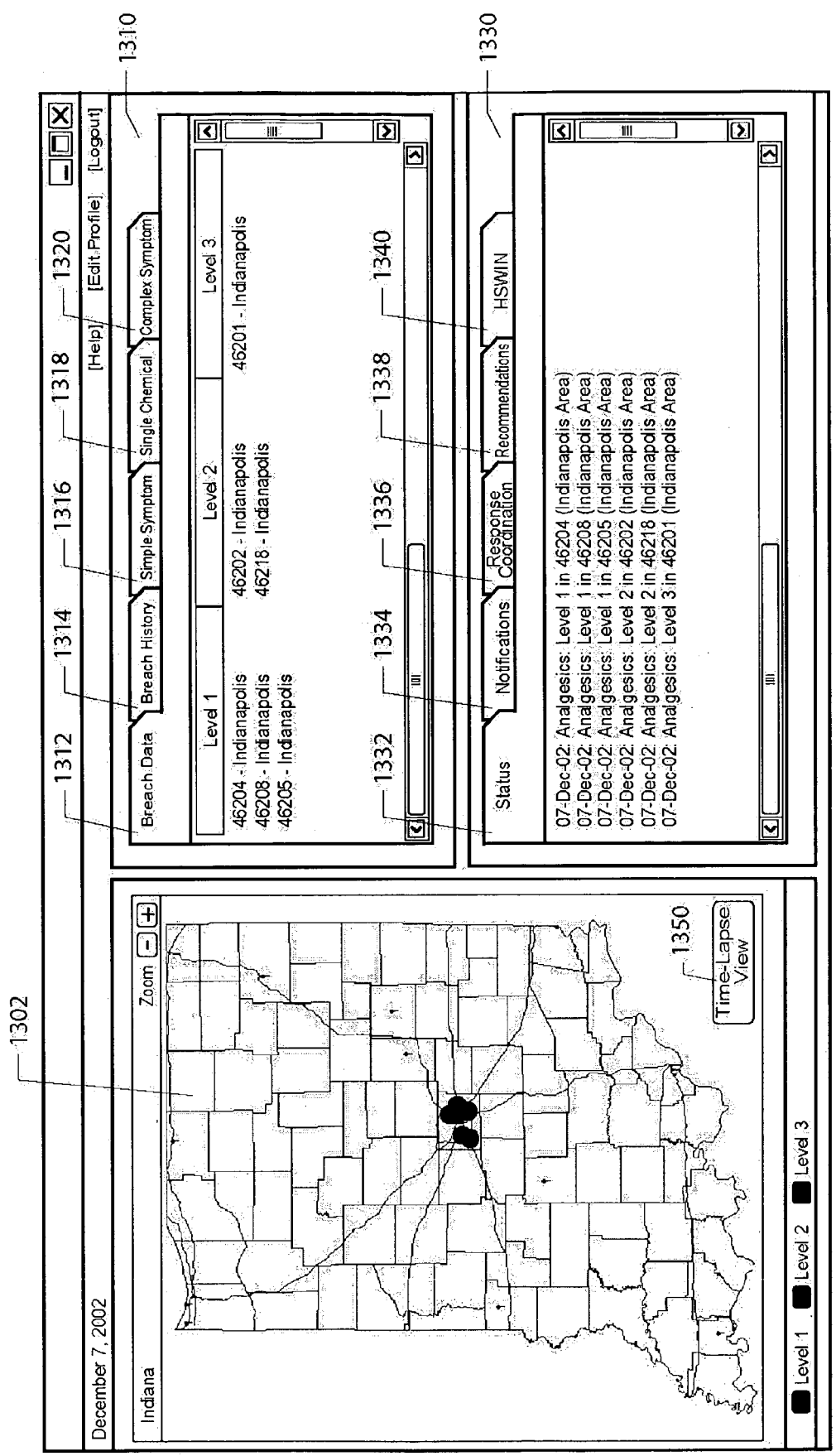
FIG. 13 is a simulated screen of a preferred embodiment showing a dashboard interface for viewing geographical information interaction, data interaction, and application interaction.

As shown in FIG. 13, the system has a dashboard layout that allows the user to view current information for the subscribed geographical entitlement area, including graphical views of the alert areas 1302, recent alerts of data breaches 1312, and current system-generated notifications 1332. The dashboard layout is divided into three primary interaction areas; the geographic information interaction section 1302, the data interaction section 1310, and the application interaction section 1330. The geographic information interaction section provides Subscribers with a representation of their geographical entitlement area as well as geographical localization and representation of system data. Additional geographic information interactivity is also available in Time-Lapse View 1350, as will be discussed with FIG. 14.

In a preferred embodiment, the data interaction section 1310 is linked to the geographic information interaction section 1302. Data and information viewed in the data interaction section 1310 is synchronized to the geographic view represented in the geographic information interaction section 1302. In a preferred embodiment, the data interaction section 1310 provides the Subscriber with the ability to interact with recent Breach Data information 1312 as well as Historic Breach Data information 1314. In the data interaction section 1310, Subscribers also are able to interact with system data by category, such as Simple Symptom 1316, Single Chemical 1318 and Complex Symptom 1320.

The application interaction section 1330 provides access to other system functionality as will as integration with other third-party applications. The Status section 1332 contains current information pertaining to the status of system data. The Notifications section 1334 provides Subscribers the opportunity to view the text from both proactive and passive notifications. The Response Coordination section 1336 is the portal for the context-sensitive tasks and actions to be accomplished. The Recommendations section 1338 contains context-sensitive recommendations for the Subscriber to follow based on system events. Designed to be configurable, additional tabs may be added to provide bidirectional integration and interaction with other related third party applications 1340.

Figure 14:
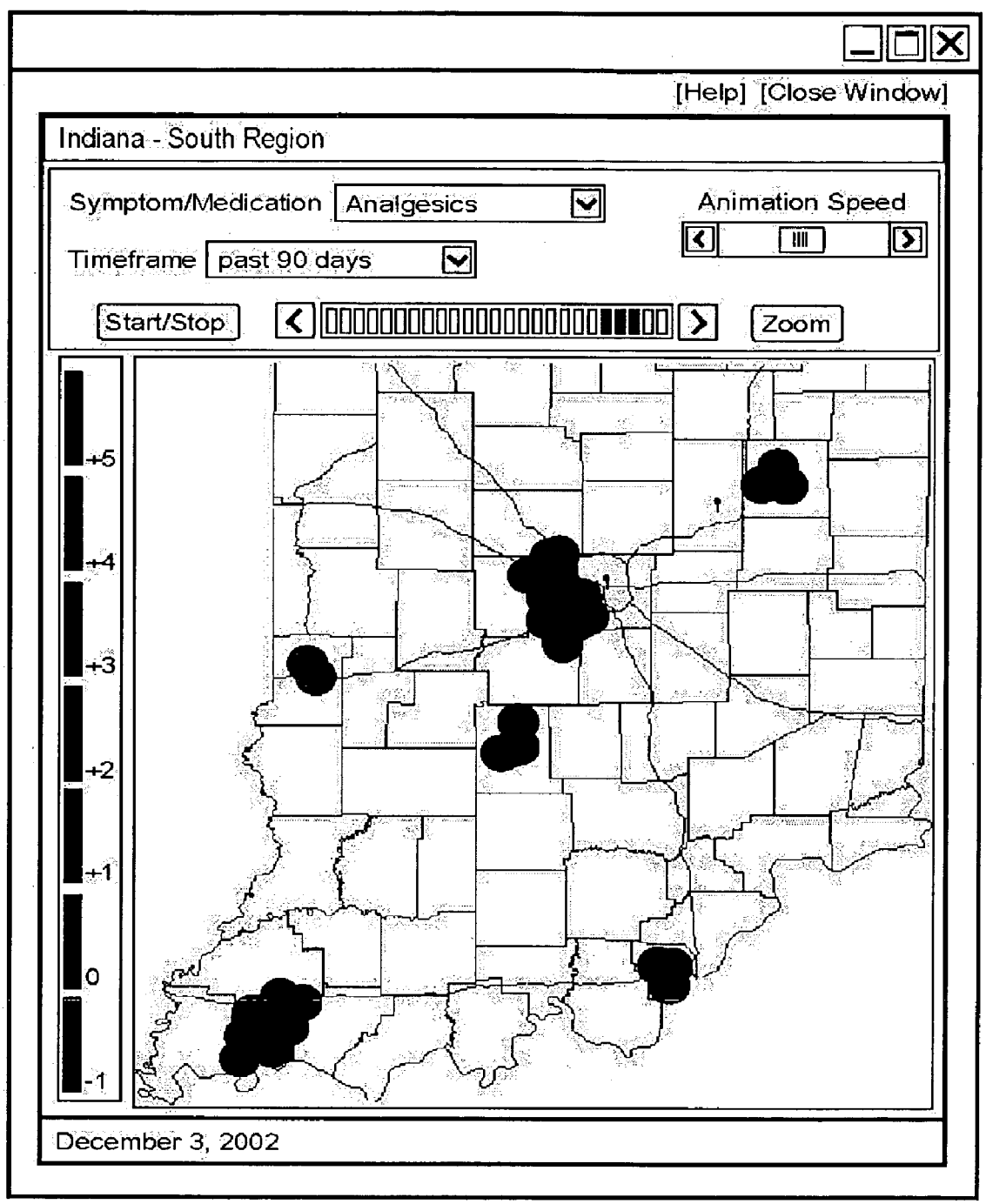
FIG. 14 is a simulated screen of a preferred embodiment showing an enlarged view of a time-lapse animation of the intensity of sales volume for any given medication category or symptom throughout a geographic area.

FIG. 14 shows a simulated screen of the geographical entitlement area in an enlarged view. In a preferred embodiment, Subscribers will have the option of viewing historical sales data in a time-lapse animation format displaying the relative intensity of sales in a particular category throughout their Geographical Entitlement Area. Subscribers will select a category or symptom, a timeframe and a geographic region. The timeframe is configurable, and in a preferred embodiment will allow the Subscriber to choose between 30, 60 and 90 days. Once the timeframe, category and geographic region are selected, the Subscriber will start the time-lapse animation. This animation is analogous to a Doppler weather radar map. The system will calculate the relative intensity of sales of each category at each retail outlet. Each intensity level will be assigned a color. For each time period to be included in the time-lapse display, the area surrounding each retail outlet will be set to the appropriate color depending on that outlet's intensity level. The time-lapse display will then display the appropriate number of snapshots of the map in an automated fashion.

The time-lapse animation displays one snapshot per time period. In a preferred embodiment, the time period is one day. The time-lapse animation monitors near real-time data. In a preferred embodiment, near real-time data refers to sales data from the previous day. Additional methods could be conceived that use older data or use constant communication channels for true real-time data.

The time-lapse display has the advantage of visually representing the intensity levels of sales of OTC medications within a particular geographic area. Subscribers are able to use this information to infer the inception, progression and strength of public illnesses based on the medications purchased by the affected consumers. Using this information, subscribers can see the areas where public illnesses have spread and what areas are likely to be affected next.

Figure 15:
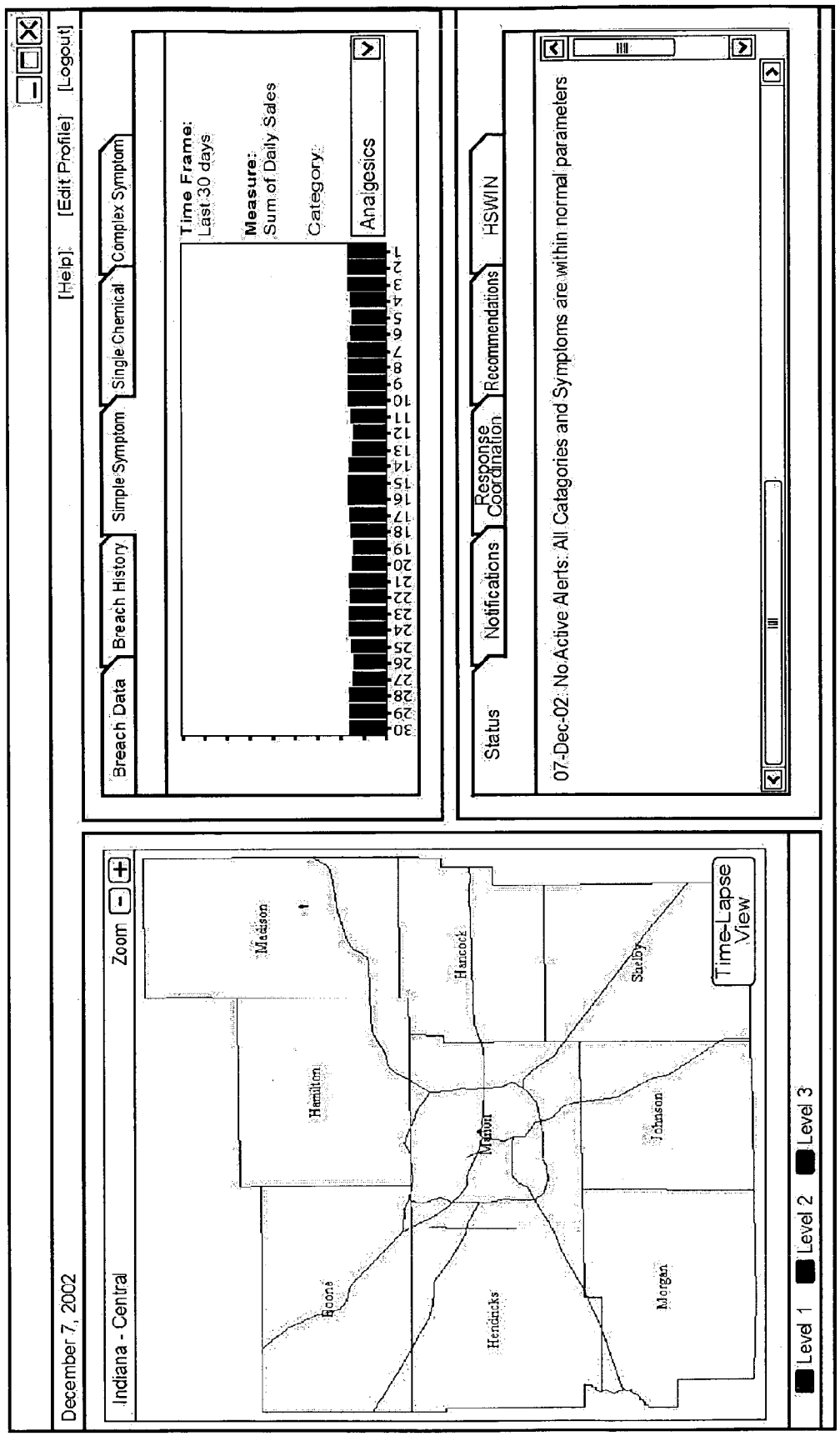
FIG. 15 is a simulated screen of a preferred embodiment showing historical trend information for the currently selected geographical area and simple symptom category.
Figure 16:
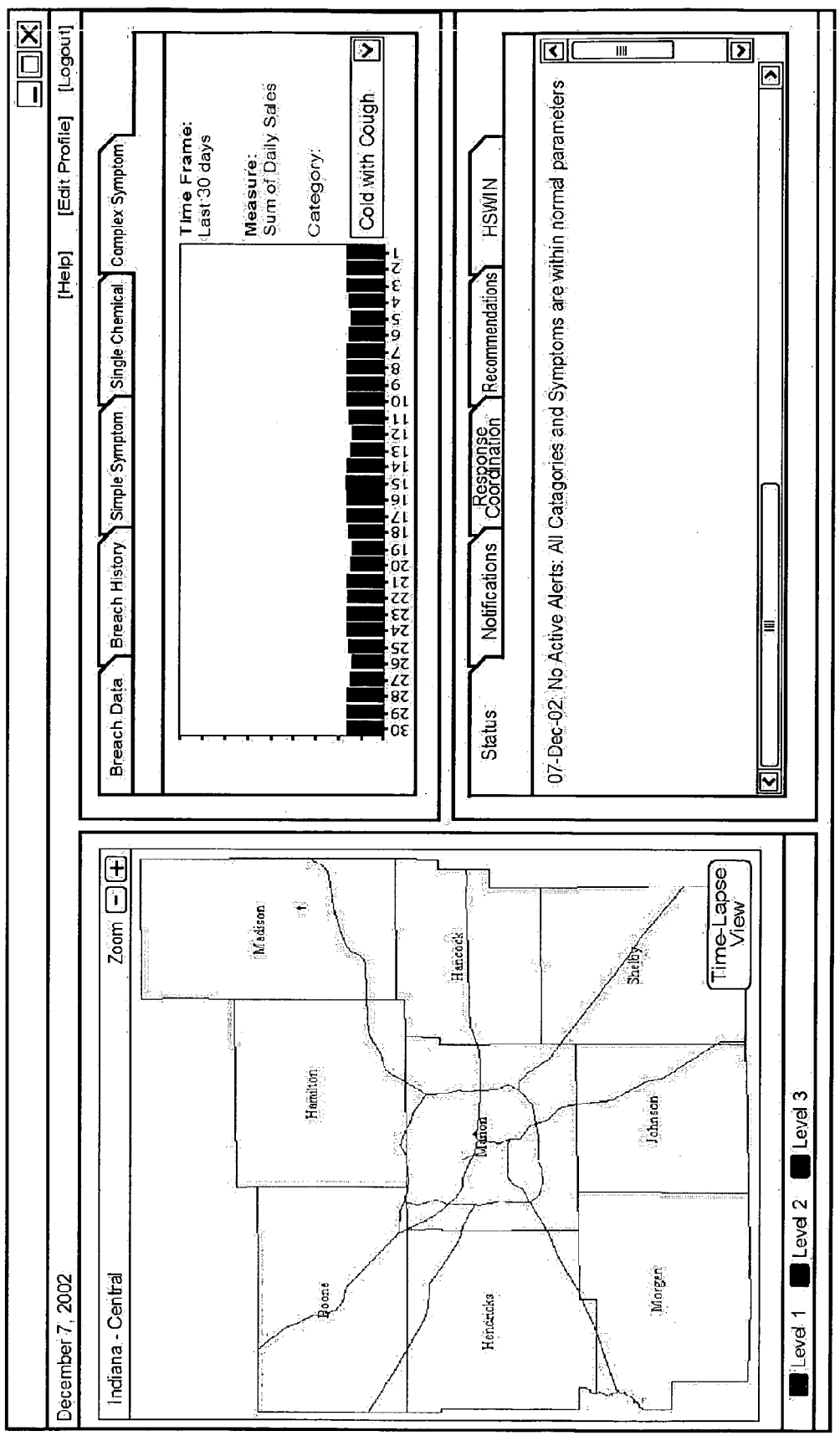
FIG. 16 is a simulated screen of a preferred embodiment showing historical trend information for the currently selected geographical area and complex symptom category.
Figure 17:
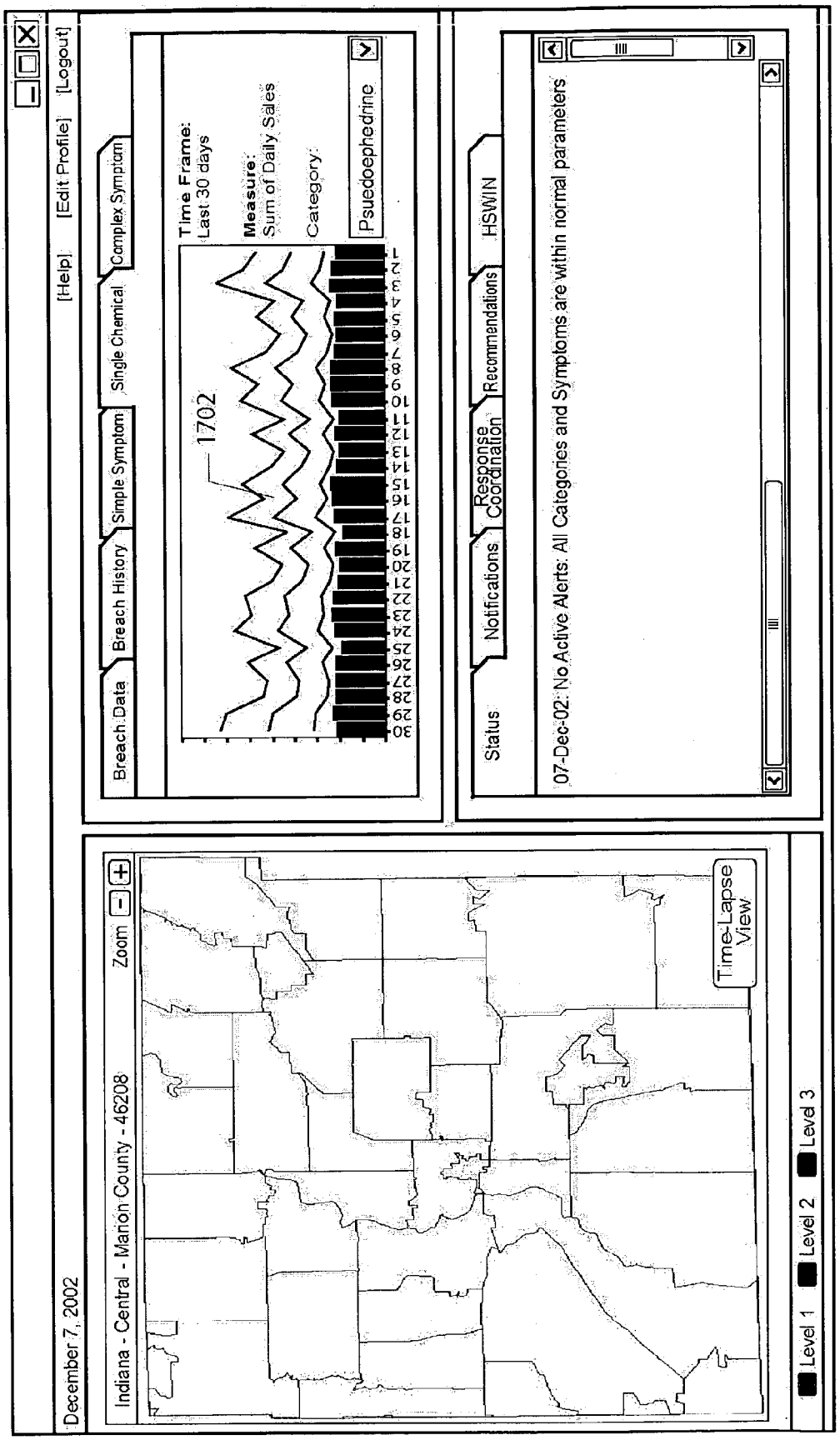
FIG. 17 is a simulated screen of a preferred embodiment showing historical trend information for the currently selected geographical area and single chemical category.

FIG. 15 is a simulated screen showing some historical trend information for the currently selected geographical area and simple symptom category. FIG. 16 shows some historical trend information for a complex symptom category. FIG. 17 is a simulated screen showing historical trend information for the currently selected geographical area and single chemical category. At the illustrated level of geographic detail, the chart in the data interaction section reflects the actual breach level thresholds for level 1, level 2 and level 3 breaches 1702.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. A person of ordinary skill in the computer software art is readily capable of practicing this invention based upon this detailed description of the preferred embodiment to date without undue experimentation. A person of ordinary skill in the computer software art will also recognize that the user interface features, including the window navigation style, mechanism for selecting options, screen content and layouts could be organized differently on the same screen or different screens than as portrayed in the illustrations and still be within the spirit of the invention.

The invention claimed is:

1. A method for identification of elevated sales of predetermined products indicative of at least one public health condition, comprising the steps of:
providing a categorization schedule to at least one party selling at least one of said predetermined products, said schedule incorporating product identifiers corresponding to said predetermined products, each of said product identifiers being associated with at least one of a plurality of aggregation categories related to at least one ingredient contained in said corresponding one of said predetermined products, wherein said at least one party uses said categorization schedule to generate information that associates sales of at least one of said predetermined products by said party with the contents of at least one of said plurality of aggregation categories;
receiving said aggregation category content information from said at least one party;
utilizing said aggregation category content information to populate at least one of a plurality of analytical categories indicative of a health condition;
determining an alert threshold for said at least one of said plurality of analytical categories;
detecting when said alert threshold for said at least one of said plurality of analytical categories is exceeded; and
generating, in response to said detecting, a notification that said alert threshold was exceeded.

2. The method of claim 1, wherein said party is a retailer.

3. The method of claim 1, wherein said party is a wholesaler.

4. The method of claim 1, wherein said generating of said notification is by e-mail.

5. The method of claim 1, wherein said generating of said notification is by telephone.

6. The method of claim 1, wherein said notification is sent to at least one recipient.

7. The method of claim 6, wherein said at least one recipient is a government agency.

8. The method of claim 6, wherein said at least one recipient is a health care facility.

9. The method of claim 6, wherein at least a second recipient is notified in the event that said at least one recipient does not respond to said notification.

10. The method of claim 1, wherein said generating of said notification is by displaying a message on a computer screen when a specified internet web site is accessed.

11. The method of claim 1 wherein the contents of said analytical categories are presented graphically based on a selected geographic region.

12. The method of claim 1, wherein the contents of said analytical categories are presented in time-lapse animation format.

13. The method of claim 1, wherein said product identifiers comprise universal product codes.

14. The method of claim 1, wherein said aggregation category content information is received in the form of an electronic file wherein said second party provides a data clearinghouse for categorized data from at least one.

15. The method of claim 1, wherein the receiver of said aggregation category content information provides a data clearinghouse for said aggregation category content information, said data clearinghouse being used to provide detection of public health conditions.

16. The method of claim 1, wherein the information contained in said analytical categories does not reveal the source of said information.

17. A system for identification of elevated sales of predetermined products indicative of at least one medical condition comprising:
a recipient module maintaining information about a plurality of information recipients;
a retail chain module maintaining information about a plurality of retail stores;
a categorization module maintaining categorization information about said predetermined products related to at least one ingredient contained in each of said predetermined products, said categorization module providing said categorization information to said plurality of retail stores to enable said plurality of retail stores to generate categorized data associated with the sale of predetermined products;
a breach module for receiving and evaluating said categorized data from said plurality of retail stores for detecting information indicative of at least one public health condition, and for establishing at least one alert threshold associated with said sales indicative information; and a notification module generating and sending at least one alert to at least one of said plurality of recipients when said at least one alert threshold has been exceeded.

18. The system of claim 17, further comprising a geographic entitlement module for maintaining geographic information related to the service area of said plurality of retail stores.

19. The system of claim 17, wherein said categorization information is further determined by at least one of the unique identifier of said predetermined product, the symptoms treated by said predetermined product, and possible causes of said symptoms.

20. The system of claim 17, wherein said alert is sent to said plurality of recipients over the Internet.

21. The system of claim 17, wherein said recipient information is determined by at least one of a recipient name, recipient contact information, a preferred method of contacting said recipient, and alternate contact information if said recipient does not respond to said alert.

22. The system of claim 17, wherein said categorization module produces at least one file containing said categorization information, and said retail chain module provides said at least one file to said at least one of said plurality of retail stores.

23. The system of claim 17, wherein said plurality of retail stores receives said categorization information in at least one text file, said information further comprising an algorithm for processing the at least one text file to generate said categorized data.

* * * * *

UNITED STATES PATENT AND TRADEMARK OFFICE
CERTIFICATE OF CORRECTION

PATENT NO. : 7,069,233 B2  Page 1 of 1
APPLICATION NO. : 10/335467
DATED : June 27, 2006
INVENTOR(S) : Todd C. Bracken and Kimberly Chowning It is certified that error appears in the above-identified patent and that said Letters Patent is hereby corrected as shown below:

In column 14, line 40, please delete the words "wherein said second party provides a data clearinghouse for categorized data from at least one" from claim 14.

Signed and Sealed this

Fourteenth Day of November, 2006

JON W. DUDAS
*Director of the United States Patent and Trademark Office*